United States Patent [19]

Kohl

[11] 4,345,911

[45] Aug. 24, 1982

[54] DIAGNOSTIC AGENT FOR THE DETECTION OF BILIRUBIN IN BODY FLUIDS AND REAGENT SUITABLE THEREFOR

[75] Inventor: Helmut Kohl, Wetter, Fed. Rep. of Germany

[73] Assignee: Behringwerke Aktiengesellschaft, Marburg an der Lahn, Fed. Rep. of Germany

[21] Appl. No.: 185,763

[22] Filed: Sep. 10, 1980

[30] Foreign Application Priority Data

Sep. 12, 1979 [DE] Fed. Rep. of Germany ....... 2936745

[51] Int. Cl.³ .............................................. G01N 33/72
[52] U.S. Cl. ................................... 23/230 B; 23/905; 23/929; 252/408; 260/141; 422/56
[58] Field of Search ..................... 23/230 B, 905, 929; 422/56; 252/408; 260/141 R; 162/162; 8/666, 668, 670

[56] References Cited

U.S. PATENT DOCUMENTS

| | | | |
|---|---|---|---|
| 3,133,051 | 5/1964 | Dreyer et al. | 8/666 X |
| 3,511,607 | 5/1970 | Green | 23/230 B |
| 3,850,576 | 11/1974 | Rittersdorf et al. | 23/230 B |
| 3,880,588 | 4/1975 | Rittersdorf et al. | 23/230 B X |

OTHER PUBLICATIONS

Reimlinger, "Reactions of 3(5)-Diazopyrazole. II", Chem. Abstr., vol. 66, 1967, No. 28706w.

*Primary Examiner*—Arnold Turk
*Attorney, Agent, or Firm*—Curtis, Morris & Safford

[57] ABSTRACT

What are disclosed are the use of a diazonium salt of pyrazole for the detection of bilirubin in body fluids, a diagnostic agent for bilirubin containing such a salt, and the specific salt 3-diazopyrazole tetrafluoroborate.

8 Claims, No Drawings

DIAGNOSTIC AGENT FOR THE DETECTION OF BILIRUBIN IN BODY FLUIDS AND REAGENT SUITABLE THEREFOR

The present invention relates to a diagnostic agent containing a diazonium salt which is useful for detecting bilirubin in body fluids to a method for detecting bilirubin using such a diazonium salt, and to certain of such salts.

The analytic determination of bilirubin with the aid of diazonium salts is a method commonly used in clinical diagnosis of liver and gallbladder diseases, as is described, by way of example, in German Pat. No. 2,240,471; German Offenlegungsschriften Nos. 2,007,013; 2,364,844; 2,013,558 and in Swiss Pat. No. 512,072. To prepare diagnostic agents of this type, a diazonium salt of high purity, for example a halogenobenzenediazonium salt, dissolved in water, is generally lyophilized and stored in a container which can be tightly closed without further additives. The diazonium salts are sufficiently stable to storage when kept at a temperature of about 0° C. with the exclusion of light and humidity.

These ideal conditions, however, cannot be applied to rapid diagnostic agents such as test strips, where a great number of the diazonium salts used hitherto would rapidly decompose yielding dark colored sequence products. The stability of the diazonium salts is, however, of decisive importance for the diagnostic value of rapid diagnostic agents, in particular test papers. Experience has shown that a slight color change of these papers used in the determination of bilirubin in urine may lead to misinterpretations with regard to the decisive physiological-pathological range of bilirubin of from 0.5 to 2 mg/dl. A color change is still more pronounced in the presence of accelerators in diagnostic agents of the above type. Accelerators are generally required to ensure a sufficiently rapid and sensitive determination of bilirubin. During the storage of the diagnostic agents the content of diazonium salts per square centimeter is moreover greatly reduced while the color changes proceed. In this aspect the useful value or the lifetime of test papers for determining bilirubin is therefore likewise greatly limited.

It is therefore necessary to prepare test papers using additives having a stabilizing effect on the diazonium salts. Suitable additives are, by way of example, the aryl-sulfonic acids or meta-phosphoric acid. Even upon addition of the stabilizers, the test papers can generally be stored for not longer than 24 months.

It was therefore an object of the present invention to surmount said disadvantages of the diagnostic agents for the determination of bilirubin, in particular as regards the diazonium salts. A diazonium salt should be provided that, during storage, would not decompose or degrade yielding colored sequence products.

This object is achieved by using a diazonium salt of pyrazole as an indicator for bilirubin.

A feature of the present invention is therefore a diazonium salt of pyrazole, preferably of 3-diazopyrazole, which is used as reagent for bilirubin. 3-diazopyrazole tetrafluoroborate is particularly preferred. A further feature of the present invention is particularly a diagnostic agent for the determination of bilirubin in body fluids, in particular in urine, consisting of an absorbent carrier, in particular paper, which is impregnated with a diazonium salt, the particular feature of this diagnostic agent residing in the use of a diazopyrazole salt as the diazonium salt. 3-diazopyrazole, in particular its tetrafluoroborate, is particularly preferred.

Further suitable reagents are other salts of diazopyrazole, for example the trifluoromethylsulfonates, arylsulfonates, chlorides, sulfates, hexachloroantimonates and tetrachlorozincates.

The test strips for use as rapid diagnostic agent for bilirubin are prepared in the following manner: An absorbent carrier, advantageously paper, is impregnated with a solution containing of from 0.01 to 0.4 M/l of the reagent according to the invention, and optionally containing from 0.1 to 3 M/l of a non-volatile acid, for example m-phosphoric acid, and an accelerator, which acts as wetting agent, for example N-ethyl-N,N-dimethyl-N-dodecyl-ammonium bromide, the latter being contained in the impregnation solution in a concentration of from 0.5 to 3%. Other wetting agents of anionic, nonionic or cationic nature may be used alternatively in the same concentration.

Comparative examinations of the product according to the present invention and of reagents of the state of the art show the unexpectedly great advantage of the present invention.

The tests were run with test papers prepared from
(1) 2,4-dichlorobenzene-diazonium tetrafluoroborate (state of the art) and with
(2) pyrazole 3-diazonium-tetrafluoroborate (present invention).

The diazonium salts are obtainable according to the method described in Weygand-Hilgetag "Organisch-chemische Experimentierkunst", 3rd edition, J. A. Barth edition, Leipzig, 1966, pages 641–643.

The papers did not contain any stabilizing sulfonic acid. Paper (1) had turned light brown upon a 10 days' storage at 4° C. and dark brown upon a storage at 50° C. Paper (2) kept under identical storage conditions remained white and color gradations could be distinctly observed, when using paper (2) in a test in practice, even with low bilirubin concentrations. When using paper (1), however, only high bilirubin concentrations could be detected. The content of diazonium salt of paper (1) during the storage period at 50° C. was reduced by 60%, whereas the concentration of diazonium salt in paper (2) was unchanged.

In a further test, papers useful in determining bilirubin were prepared without the use of meta-phosphoric acid and of sulfonic acid. Paper (2) contained the pyrazole 3-diazonium-tetrafluoroborate according to the invention, whereas paper (1) contained 2,4-dichlorobenzene-diazonium tetrafluoroborate. Upon 10 days' storage at 50° C. paper (1) had turned dark brown and no longer reacted with bilirubin, whereas paper (2) had turned slightly yellow only and was still suitable for a differentiating determination of bilirubin. Diazonium salt could no longer be found on paper (1). In paper (2) the content of diazonium salt had decreased by only 10%.

Test papers containing pyrazole 3-diazonium salt and a quarternary ammonium salt as the accelerator exhibited a further advantage in the test for utility, as compared to the papers known hitherto: The new diazonium salt reacts with indicans very slowly. The test zones remain nearly colorless in urine free from bilirubin, whereas the test zones turn yellow when using halogenated diazonium salts. In the latter case color changes can be perceived only with difficulty owing to this ground color.

The following example illustrates the invention:

EXAMPLE

(1) Preparation of pyrazole 3-diazonium-tetrafluoroborate 1 mol of 3-aminopyrazole is mixed with
1 liter of diethyl ether. While stirring there is carefully added dropwise in subsequent steps
1 mol of fluoroboric acid and
1.1 mol of isopentylnitrite dissolved in
1 liter of diethyl ether.

The precipitate obtained is pyrazole 3-diazonium-tetrafluoroborate.

(2) Preparation of a test paper for bilirubin

In 1 liter of water there are dissolved
10 g of m-phosphoric acid
50 g of citric acid
30 g of dodecylbenzenesulfonate and
20 g of pyrazole 3-diazoniumtetrafluoroborate.

A paper of the type Schleicher and Schüll 2316 is impregnated with the solution obtained. The paper is dried at 50° C., whereupon it is white in color. When used in a test, it exhibits the above-described effects.

If desired, up to 100 g of naphthalene 1,5-disulfonic acid or a further stabilizer may be added to the batch.

Instead of dodecylbenzenesulfonate, another anionic or cationic wetting agent may alternatively be used, such as N-ethyl-N,N-dimethyl-N-dodecyl-ammonium bromide.

What is claimed is:

1. A diagnostic agent for the determination of bilirubin in a body fluid, said agent comprising a diagnostically effective amount of a diazonium salt of pyrazole in an absorbent carrier impregnated therewith.

2. A diagnostic agent as in claim 1 wherein said absorbent carrier is paper.

3. A diagnostic agent as in claim 1 wherein said diazonium salt is a salt of 3-amino-pyrazole.

4. A diagnostic agent as in claim 3 wherein said diazonium salt is 3-diazopyrazole tetrafluoroborate.

5. A method for detecting bilirubin in a body fluid, which method comprises contacting said body fluid with a diazonium salt of pyrazole and observing for a color change indicative of the presence of bilirubin.

6. A method as in claim 5 wherein said body fluid is urine.

7. A method as in claim 6 wherein said diazonium salt is a salt of 3-amino-pyrazole.

8. A method as in claim 7 wherein said diazonium salt is 3-diazopyrazole tetrafluoroborate.

* * * * *